United States Patent [19]

Bhat et al.

[11] 4,118,508

[45] Oct. 3, 1978

[54] PHARMACOLOGICALLY EFFECTIVE SUBSTANCE FROM PLANTS BELONGING TO THE FAMILY OF LABIATAE

[75] Inventors: Sujata Vasudev Bhat, Thana; Noel John de Souza, Bombay; Horst Dornauer, Bombay; Bani Kanta Bhattacharya, Bombay; Alihussein Nomanbhai Dohadwalla, Bombay, all of India

[73] Assignee: Hoechst Aktiengesellschaft, Frankfurt am Main, Fed. Rep. of Germany

[21] Appl. No.: 791,020

[22] Filed: Apr. 26, 1977

[30] Foreign Application Priority Data

Sep. 8, 1976 [DE] Fed. Rep. of Germany ....... 2640275

[51] Int. Cl.$^2$ ..................... A61K 31/35; C07D 311/02
[52] U.S. Cl. .................................. 424/283; 260/345.2
[58] Field of Search ...................... 260/345.2; 424/283

[56] References Cited

U.S. PATENT DOCUMENTS 3,631,039  12/1971  Andrews et al. ................. 260/345.2

OTHER PUBLICATIONS

Li, "Chinese Herbal Medicine", pp. 88, 89, 93, (1974), (Dhew Publication No. (N1H), 75–732).

*Primary Examiner*—Nicky Chan
*Attorney, Agent, or Firm*—Curtis, Morris & Safford

[57] ABSTRACT

This invention relates to a pharmacologically effective substance named Coleforsin, to a process for its preparation from plants belonging to the Labiatae family, and to pharmaceutical preparations containing it.

3 Claims, No Drawings

PHARMACOLOGICALLY EFFECTIVE SUBSTANCE FROM PLANTS BELONGING TO THE FAMILY OF LABIATAE

This invention relates to a pharmacologically effective substance named Coleforsin, to a process for its preparation from plants belonging to the Labiatae family, and to pharmaceutical preparations containing it.

The Labiatae family comprises 180 genera with about 3,500 plant species. There are especially named *Plectranthus, Coleus, Anisochilus, Lavandula and Leonitis.* About 30 *Plectranthus* species grow in India, of which *P. macranthus, P. mollis, P. stocksii, P. coetsa* and *P. incanus* are the more common plants. Moreover, there are about 9 *Coleus* species to be found in India, i.e. *C. amboinicus, C. forskohlii, C. malabaricus, C. parviflorus, C. spicatus, C. rotundifolius, C. scutellaricides, C. blumei* and *C. lacinatus.* Among the 13 species of the Anisochilus group reported to grow in India, *A. carnosus* and *A. verticillatus* are the more common plants. The plants of interest in the Lavandula genus are *L. bipinatta, L. officinalis, L. gibsoni* and *L. burmanni. Leonitis nepetaefolia* is the more common plant of the two Leonitis species growing in India.

The present invention provides a process for the preparation of Coleforsin from the aforesaid plants of the Labiatae family, more particularly from *Coleus forskohlii.*

*Coleus forskohlii* is an Indian herb belonging to the Labiatae family and is synonymous with *Coleus barbatus* (Benth.). The plants grow in different parts of India and are commonly found in the subtropical Himalayan region, the Deccan peninsula, Gujarat, Bihar and South India. The plants are also cultivated in several places in India, namely Bombay, Gujarat and Saurashtra. The morphological details and distribution of Coleus forskohlii have been described (cf. The Wealth of India, Vol II, C.S.I.R., India, 1950, page 308)

Coleforsin is a pharmacologically effective substance which has principally blood pressure lowering and positive inotropic properties. It is obtained preferably from the roots of *Coleus forskohlii.*

It is, therefore, an object of the present invention to provide a process for the preparation of Coleforsin from *Coleus forskohlii* which comprises (a) extracting ground plants of *Coleus forskohlii* with solvents such as aromatic hydrocarbons, aliphatic and aromatic halohydrocarbons, dialkyl ethers, dialkyl ketones, alkanols, carboxylic acids and their esters, or any solvent which will dissolve the desired substance, such solvents being, for example, dimethyl formamide, dioxane, tetrahydrofuran, and dimethyl sulfoxide, to obtain a solution, (b) concentrating the extract solution to obtain a residue, (c) treating the residue with a solvent and/or solvent mixture chosen on the basis of the differences in solubility of the residue in different solvents to obtain a crude product, (d) treating the crude product with a base, whereby a crude terpenoid mixture is obtained, (e) optionally subjecting the crude terpenoid mixture to a chromatographic separation to obtain a semi-pure terpenoid, and (f) recrystallizing the crude terpenoid mixture or the semi-pure terpenoid to obtain Coleforsin.

The following flow scheme illustrates the process of the invention.

Chart I

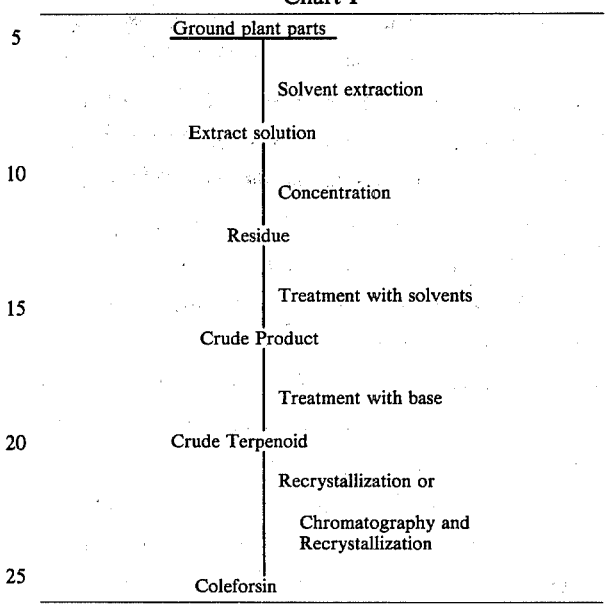

It is suitable to use as a starting product the dried and ground roots of *Coleus forskohlii,* which are preferably subjected to a previous extraction with a hydrocarbon in order to remove the main portion of plant fats and waxes contained in the roots. There are preferably used hydrocarbons having from 5 to 7 carbon atoms, for example petroleum ether, pentane or hexane, in a ratio of 1:2 to 1:10 parts by weight of plant material to solvent.

For extracting the desired substance from *Coleus forskohlii,* aromatic hydrocarbons or aliphatic halohydrocarbons having from 1 to 3 carbon atoms and up to 3 halogen atoms, preferably up to 3 chlorine atoms, or a lower alkanol having from 1 to 6 carbon atoms are preferably used; benzene, toluene or xylene, methylene chloride or chloroform, methanol or ethanol being preferred. The extracting agents are preferably used in a ratio of 1:2 to 1:10 parts by weight of plant material to extracting agent. The extraction may be carried out at a temperature ranging from ambient to the boiling point of the solvent used for extraction, preferably 30°–40° C.

The extract solution is concentrated under reduced pressure, preferably in vacuo, to give a residue.

Depending on the type of solvent used for the extraction and the solubility properties of the residue, various methods can be used to work up the residue. Some of the preferred procedures for the treatment of the residue to obtain the crude products are illustrated by the following charts II, III and IV.

Chart II

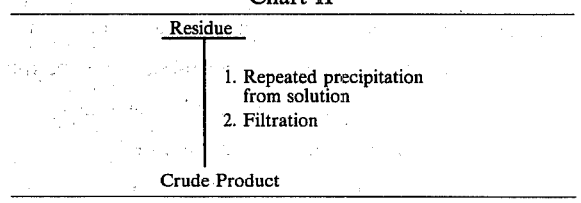

Referring to Chart II, when the plant material is extracted with an aromatic hydrocarbon, for example benzene or toluene or an aliphatic halohydrocarbon, for example chloroform, the residue obtained from the extract solution is repeatedly precipitated by the addition of solvents in which the residue or a portion thereof is insoluble. The residue can be dissolved, for example, in the least amount of a solvent such as an aromatic hydrocarbon, preferably benzene or toluene, a halohydrocarbon, preferably chloroform, or an ester, preferably ethyl acetate, at a temperature ranging from ambient to the boiling point of the solvent used, preferably 30° to 40° C. To the solution obtained a non-solvent is then added such as an aliphatic hydrocarbon having from 5 to 7 carbon atoms, preferably petroleum ether, pentane or hexane, until precipitation is complete. The suspension is allowed to stand until the precipitate settles, the supernatant liquid is removed, and the residue is resubjected three times to the procedure of dissolution and precipitation. The precipitate is finally filtered to give a crude product.

Chart III

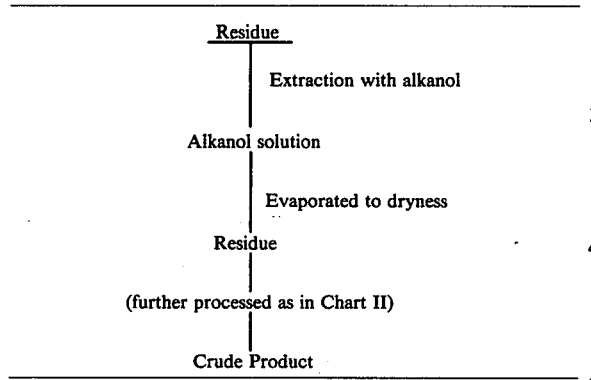

Referring to Chart III, the residue obtained from the aromatic hydrocarbon extract or halohydrocarbon extract of the plant is treated with a lower alkanol having from 1 to 6 carbon atoms, for example methanol or ethanol which are preferred, until all alkanol soluble material has been dissolved.

The alkanol is preferably used in an amount of from 10 to 40 parts by weight for each part by weight of residue. The extraction can be carried out at a temperature ranging from ambient to the boiling point of the solvent used, preferably 30° to 40° C. The alkanol extracts are combined, filtered and evaporated to dryness under reduced pressure, preferably in vacuo. To obtain the crude product the residue can be further processed by the procedures described above for Chart II.

Chart IV

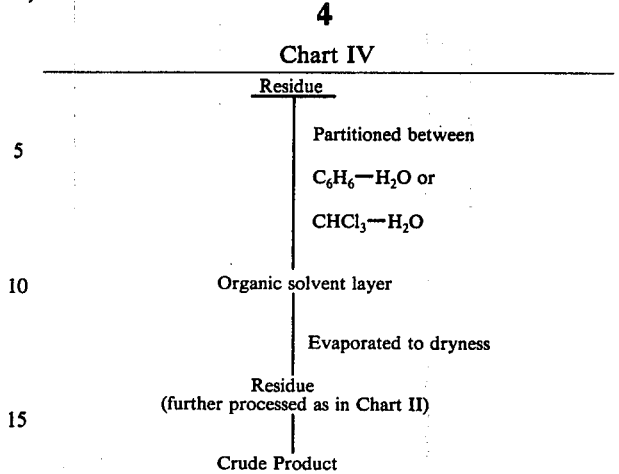

According to Chart IV, the residue obtained by extraction with an alkanol, for example methanol or ethanol, is partitioned between two immiscible solvents, one of which is capable of dissolving the desired substance, for example an aromatic hydrocarbon, preferably benzene, or an aliphatic or aromatic halohydrocarbon, preferably chloroform, and water. Benzene or chloroform and water are preferably used in a ratio of about 1:1 part by volume. The organic layer is separated and dried and the solution is evaporated to dryness under reduced pressure, preferably in vacuo. The residue obtained can be processed further as described for Chart II to a crude product.

The crude product obtained by any of the processes illustrated by Charts II, III and IV is subjected to a treatment with a base according to one of many possible procedures. Some of the preferred procedures are described below.

The crude product is treated with an alkali metal alkoxide, preferably sodium methoxide and sodium ethoxide, in the presence of a solvent, for example an ether, preferably dioxane, tetrahydrofuran or diethyl ether, at a temperature in the range from ambient to the boiling point of the solvent used, preferably 30° to 40° C. The pH of the solution is adjusted to 5 to 7 by adding on organic acid, for example acetic acid, or an inorganic acid, for example hydrochloric acid, the solution is concentrated, diluted with water and the mixture of crude terpenoids is filtered off.

According to another method, the crude product is treated with an alkali metal carbonate, preferably sodium or potassium carbonate, or an alkali metal bicarbonate, preferably potassium bicarbonate, in the presence of a solvent, for example an alkanol having from 1 to 6 carbon atoms, preferably methanol or ethanol, or an aqueous alkanol, at a temperature in the range from ambient to the boiling point of the solvent used, preferably 30° to 40° C. The solution obtained is concentrated, diluted with water and the mixture of crude terpenoids is filtered off.

According to a third method, the crude product is treated with a basic metal oxide, for example basic alumina, in the presence of a solvent, preferably an aromatic hydrocarbon, especially benzene or toluene, or an ether, preferably diethyl ether, dioxane, or tetrahydrofuran, at a temperature in the range from ambient to the boiling point of the solvent used, preferably 30° to 40° C. The suspension obtained is filtered and the metal oxide repeatedly treated with an organic solvent, preferably ethyl acetate, acetone, chloroform, methanol, ethanol and/or a mixture of any two or more of the said solvents, and the resulting extracts are evaporated to dryness under reduced pressure, preferably in vacuo, to give a mixture of crude terpenoids.

The mixture of crude terpenoids obtained by any one of the processes described above can be subjected to chromatographic separation. Due to the differences in chromatographic mobility and by the visualization of terpenoids with spray reagents, for example vanillin-sulfuric acid or anisaldehydesulfuric acid, a semi-pure terpenoid can be obtained. Either the mixture of crude terpenoids obtained prior to chromatographic separation or the semi-pure terpenoid after chromatographic separation can be recrystallized from solvents, for example ethyl acetate, chloroform or benzene, each in admixture with an aliphatic hydrocarbon having from 5 to 7 carbon atoms, preferably petroleum ether, hexane or pentane, to obtain Coleforsin, the compound of the invention, having a melting point of 208° to 211° C.

The active substance Coleforsin has the molecular formula $C_{22}H_{34}O_7$, which has been computed from the molecular weight of 410 mass units determined by mass spectroscopy and the following data of elemental analysis: found C = 64 to 65%; H = 8–8.5%; calculated C = 64.37%; H = 8.35%.

The ultraviolet spectrum shows absorption maxima at wavelengths of 208 to 210 nm ($\epsilon$max. 1,000 to 1,200) and 305 to 310 nm ($\epsilon$max 45 to 50).

In the accompanying drawing are shown the infrared spectrum (FIG. 1) and the nuclear magnetic resonance spectrum (FIG. 2). The optical rotation $[\alpha]_D$ depends on the solvent in which the measurements are performed, the values in methanol being in the range of from +15 to +25 (c = 2.8 in $CH_3OH$).

Coleforsin is soluble in organic solvents such as methanol, ethanol, propanol, acetone, chloroform, methylene chloride, ethyl acetate, benzene, ether, dioxane, tetrahydrofuran, dimethyl formamide and dimethylsulfoxide.

Coleforsin has physical and chemical properties usually shown by terpenoids. The results of spectral and chemical analysis reveal that Coleforsin is a terpenoid possessing the following carbon skeleton.

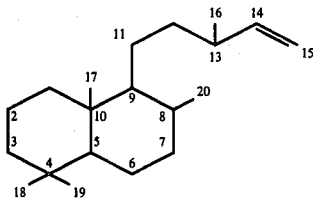

bearing oxygen-containing functional groups and carrying substituents in such a way that it has the following structural elements: (a) two secondary hydroxy groups, (b) one tertiary hydroxy group, (c) one oxide group, (d) one acetoxy group and (e) one keto group.

The spectroscopical and chemical data indicate for Coleforsin the following structure

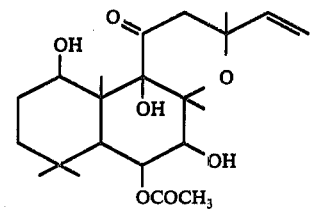

the formula including all possible stereoisomers of the compound.

The compound of the invention is characterized by a very good hypotensive effect. Moreover, it has a vasodilating effect on peripheral vessels and a positive inotropic acitivity.

Owing to its hypotensive effect Coleforsin can be used in the treatment of heart and circulatory diseases, for example essential and malignant hypertonia, myovascular insufficiency, Angina pectoris, and disorders in the peripheral circulation. In therapy, the compound can be used in combination with other pharmacologically active substances, for example diuretics, antiarrhythmics, $\beta$-blockers, tranquillizers, coronary dilating substances, hypolipidemics and so on.

Owing to its positive inotropic activity, the compound of the invention is suitable for the treatment of myovascular insufficiency, collapse due to hemorrhage, and shock.

The compound of the invention can be administered perorally or intravenously. Depending on the severity of the disease and the weight of the patient, the daily dose varies between 25 and 1,000 mg.

For peroral administration tablets or dragees containing 25 to 1,000 mg of active compound and the usual auxiliaries and carrier materials such as talcum, starch, lactose, are preferably used. For intravenous administration the active compound is dissolved or suspended in a pharmaceutically tolerated plant oil, for example peanut oil or sesame oil, or it is dissolved in an alcohol such as ethanol, propanediol, glycerol or a mixture thereof.

The following examples illustrate the invention.

EXAMPLE 1

Dried and ground roots of *Coleus forskohlii* (12 kg) were extracted twice with 25 l. portions of petroleum ether (b.p. 60°–80°). The roots were then repeatedly extracted with 25 l. portions of benzene at a temperature of 35°–40° C. till they were exhaustively extracted. 100 l. of benzene were used. The combined benzene extracts were filtered and evaporated in vacuo. The residue (about 300 g) was dissolved in about 60 ml of benzene and about 1 l. of petroleum ether (b.p. 60°–80°) was added with stirring. A precipitate separated. The suspension was allowed to settle, the supernatant layer was removed and the residue was resubjected three times to the process of dissolution in benzene and precipitation with petroleum ether. After the third precipitation, the precipitate was filtered and dried.

To a stirred solution of the precipitate (7.0 g) in dry dioxane (140 ml) sodium methylate (1.0 g) was added and the solution was stirred at room temperature for 1 hour. A solution of acetic acid was added to the solution till the pH was adjusted to a value of about 5, the solvent was evaporated in vacuo, water was added, the mixture was chilled at 0.5° C. for ½ hr., and the resulting precipitate was filtered. The precipitate (about 6.0 g) was chromatographed on a column of silica gel. The appropriate chromatography fractions, as indicated by monitoring the eluted fractions by thin layer chromatography wherein visualisation was carried out with spray reagents specific for terpenoids, for example vanillin-sulfuric acid, were combined and evaporated to dryness in vacuo. The residue was re-crystallised from ethyl acetate-petroleum ether (b.p. 60°-80°) to give colorless crystals of Coleforsin.

EXAMPLE 2

Dried, ground and defatted roots of *Coleus forskohlii* were extracted with benzene, the extract was concentrated and the residue was repeatedly precipitated from its solution in benzene with petroleum ether as described in the first paragraph of Example 1.

Potassium carbonate (1.4 g) was added to a solution of the precipitate (6.0 g) in 80% aqueous methanol (200 ml) and the solution was stirred for one hour at room temperature. The solution was concentrated to about 1/10 its volume and water was added to give a precipitate. The precipitate was filtered and recrystallised from chloroform-petroleum ether (b.p. 60°-80° C.) to give colorless crystals of Coleforsin.

EXAMPLE 3

Dried, ground and defatted roots of *Coleus forskohlii* were extracted with benzene, the extract was concentrated and the residue was repeatedly precipitated from its solution in benzene with petroleum ether as described in the first paragraph of Example 1.

90 g of alumina were added to a solution of the precipitate (6.0 g) in benzene (150 ml) and the suspension was stirred at room temperature. The benzene layer was filtered and the alumina was repeatedly extracted by trituration with ethyl acetate-methanol (95:5). The combined ethyl acetate-methanol (95:5) extracts were evaporated to dryness in vacuo. The residue was recrystallised from benzene-petroleum ether (b.p. 60°-80°) (1:5) to give colorless crystals of Coleforsin.

EXAMPLE 4

Dried and ground roots (12 kg) of *Coleus forskohlii* were extracted with 25 l. portions of chloroform till they were exhaustively extracted. 75 l. of chloroform were used. The combined chloroform extracts were filtered and evaporated in vacuo. The residue (about 300 g) was stirred thrice with 1.5 l. portions of methanol and filtered. The filtrate was evaporated to dryness to give a gummy residue (about 200 g). The residue was processed further as described in Examples 1, 2 and 3 for the residue from the benzene extract of the plant.

EXAMPLE 5

Dried and ground whole plant material of *Coleus forskohlii* (12 kg) was repeatedly extracted with 25 l. portions of methanol till it was exhaustively extracted. 100 l. of methanol were used. The combined methanol extracts were filtered and evaporated in vacuo. The residue (about 650 g) was partitioned between 2 l. chloroform and 1.5 l. water. The chloroform layer was separated. The aqueous layer together with the interphase between the aqueous and chloroform layers was extracted repeatedly with 1.5 l. portions of chloroform and the chloroform layer was separated. The combined chloroform extracts were filtered, dried over anhydrous sodium sulfate and evaporated in vacuo to give a gummy residue (about 300 g). The residue was processed further according to the procedure described in Examples 1, 2 and 3 for the residue obtained from the benzene extract of the plant.

What is claimed is:

1. A compound, in purified and isolated form, having a melting point from 208° C. to 211° C., the molecular formula $C_{22}H_{34}O_7$, and the structural formula

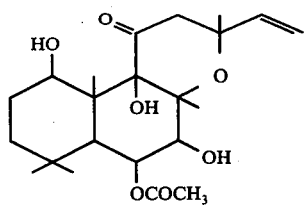

2. A pharmaceutical preparation for the treatment of cardiac or cardiovascular diseases comprising an effective amount therefor of a substance as in claim 1 in combination with a pharmaceutical carrier.

3. A method for treating cardiac or cardiovascular diseases in a patient suffering therefrom, which comprises orally or intravenously administering an effective amount therefor of a substance as in claim 1.

* * * * *